United States Patent [19]

Munroe et al.

[11] Patent Number: 5,597,694
[45] Date of Patent: Jan. 28, 1997

[54] INTERSPERSED REPETITIVE ELEMENT-BUBBLE AMPLIFICATION OF NUCLEIC ACIDS

[75] Inventors: David J. Munroe, Somerville; David E. Housman, Newton, both of Mass.

[73] Assignee: Massachusetts Institute of Technology, Cambridge, Mass.

[21] Appl. No.: 133,629

[22] Filed: Oct. 7, 1993

[51] Int. Cl.$^6$ .............................. C12Q 1/68; C12P 19/34
[52] U.S. Cl. .................... 435/6; 435/91.1; 435/91.2; 435/91.5; 435/810; 436/501; 536/22.1; 536/23.1; 536/24.1; 536/24.3; 536/24.31; 536/24.32; 536/24.33; 935/77; 935/78; 935/88
[58] Field of Search ........................ 435/6, 91.1, 91.2, 435/91.5, 810; 436/501; 536/22.1, 23.1, 24.1, 24.3–33, 25.4; 935/77, 78, 88

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,215,899 | 6/1993 | Dattagupta | 435/6 |
| 5,411,875 | 5/1995 | Jones | 435/91.2 |

FOREIGN PATENT DOCUMENTS

| | | |
|---|---|---|
| 0237362 | 9/1987 | European Pat. Off. |
| 0236069 | 9/1987 | European Pat. Off. |
| 0258017 | 3/1988 | European Pat. Off. |
| 0430402A2 | 6/1991 | European Pat. Off. |
| 0511750A1 | 11/1992 | European Pat. Off. |
| 2221909 | 2/1990 | United Kingdom. |
| WO90/08821 | 8/1990 | WIPO. |

OTHER PUBLICATIONS

Suijkerbuijk, R. et al., "Fluorescent in Situ Identification of Human Marker Chromosomes Using Flow Sorting and Alu Element–Mediated PCR", Genomics, 13, pp. 355–362, (1992).

Breen, M. et al., "YAC Mapping by FISH Using Alu–PCR Generated Probes", Genomics, 13, pp. 726–730, (1992).

Zucman, J. et al., "Rapid Isolation of Cosmids from Defined Subregions by Differential Alu–PCR Hybridization on Chromosome 22–Specific Library", Genomics, 13, pp. 395–401, (1992).

Brooks–Wilson, A. et al., "Human Repeat Element–Mediated PCR: Cloning and Mapping of Chromosome 10 DNA Markers", Genomics, 13, pp. 409–414 (1992).

Ledbetter, S. et al., "Rapid Isolation of DNA Probes within Specific Chromosome Regions by Interspersed Repetitive Sequence Polymerase Chain Reaction", Genomics, 6, pp. 475–481, (1990).

Brooks–Wilson, A. et al., "Rapid Cloning and Characterization of New Chromosome 10 DNA Markers by Alu Element–Mediated PCR", Genomics, 7, pp. 614–620, (1990).

(List continued on next page.)

Primary Examiner—Ardin H. Marschel
Attorney, Agent, or Firm—Wolf, Greenfield & Sacks, P.C.

[57] ABSTRACT

A method for amplifying a nucleic acid fragment is described. A nucleic acid having interspersed repetitive elements is cleaved and the resulting nucleic acid fragments are ligated to a bubble oligonucleotide having two double stranded portions flanking a non-complementary portion consisting of two single strands to make bubble/nucleic acid units. These units are treated with a first primer that is complementary to at least a portion of the interspersed repetitive element, and with a second primer that is complementary to at least a portion of the extension product of the first primer, that portion containing sequences complementary to one of the single strands of the bubble oligonucleotide, under conditions which produce extension products of the primers. Also described are methods for labeling the products of the amplification, methods for detecting chromosomal aberrations and other uses of the amplification products.

34 Claims, 3 Drawing Sheets

OTHER PUBLICATIONS

Lichter, P. et al., "Fluorescence in situ hybridization with Alu and L1 polymerase chain reaction probes for rapid characterization of human chromosomes in hybrid cell lines", Proc. Natl. Acad. Sci. USA, vol. 87, pp. 6634–6638, (Sep. 1990).

Pinkel, D. et al., "Fluorescence in situ hybridization with human chromosome-specific libraries: Detection of trisomy 21 and translocations of chromosome 4", Proc. Natl. Acad. Sci. USA, vol. 85, pp. 9138–9142, (Dec. 1988).

Cotter, F. et al., "The Generation of DNA Probes to Chromosome 11q23 by Alu PCR on Small Numbers of Flow-Sorted 22q-Derivative Chromosomes", Genomics, 9, pp. 473–480, (1991).

Lengauer, C. et al., "Painting of human chromosomes with probes generated from hybrid cell lines by PCR with Alu and L1 primers", Hum Genet, 86, pp. 1–6, (1990).

Riley, J. et al., "A novel, rapid method for the isolation of terminal sequences from yeast artificial chromosome (YAC) clones", Nucleic Acids Research, vol. 18, No. 10, pp. 2887–2890, (1990).

Nelson, D. et al., "Alu PCR: The Use of Repeat Sequence Primers for Amplification of Human DNA from Complex Sources", in PCR Technology: Principles and Applications for DNA Amplification; ed. H. A. Erlich, Stockton Press, pp. 113, 118 (1989).

Nelson, D. et al., "Alu polymerase chain reaction: A method for rapid isolation of human-specific sequences from complex DNA sources", Proc. Natl. Acad. Sci. USA, vol. 86, pp. 6686–6690, (1989).

Ou et al., "DNA Amplification for Direct Detection of HIV-1 in DNA of Peripheral Blood Mononuclear Cells", Science, 239, pp. 297–301 (1988).

Lengauer, C. et al., "Chromosomal bar codes produced by multi-color fluorescence in situ hybridization with multiple YAC clones and whole chromosome painting probes", Human Molecular Genetics, vol. 2, No. 5, pp. 505–512, (1993).

```
                                              AGAAGGGAGAG                    TCTTCCCTCTC
                                             /                              /
                    GCTGTCTGTCGAAGGTAAACGGACGAG          TTTACGATACAACTGCTTGAGGCCGGCG          TTTACGATACAACTGCTTGAGGCCGGCG
                   /                                   /
        GAAGGAGAGGAC                      CTTCCTCTCCCTG
```

Fig. 3

INTERSPERSED REPETITIVE ELEMENT-BUBBLE AMPLIFICATION OF NUCLEIC ACIDS

The U.S. Government has a paid-up license in this invention and the right in limited circumstances to require the patent owner to license others on reasonable terms as provided for by the terms of Grant No. 1 F32 CA 08775-01 awarded by the National Cancer Institute and Grant No. HG00299 awarded by the National Institutes of Health.

FIELD OF THE INVENTION

This invention relates to amplification of nucleic acid sequences, labeling products of the amplification, and diagnostic and other uses thereof.

BACKGROUND OF THE INVENTION

The ability to rapidly and efficiently generate a representative set of single copy sequences targeted to specific segments of the genome is important for genomic studies and cytogenetic analysis of chromosomal aberrations associated with genetic disorders, cancers and other diseases.

Traditional polymerase chain reaction (PCR) amplification methods have required knowledge of the sequences flanking both sides of the region that is to be amplified, so that the flanking sequences can serve as primers for the amplification procedure. Such a requirement has severely restricted use of this type of PCR as a method for generating amplification products from any region of the genome that is desired.

Using interspersed repetitive element (IRE) PCR procedures (referred to as inter-IRE PCR), in which both of the primers are derived from an IRE with known sequence, specific amplification of certain human genomic DNA sequences contained within somatic cell hybrids, yeast artificial chromosomes (YACs), cosmids and phage vectors have been reported. Inter-IRE PCR, however, is limited in that it will occur only between pairs of IRE sequences which are at an appropriate distance and orientation with respect to each other. The utility of inter-IRE PCR is further restricted by the apparent asymmetric distribution of repeat sequences within the genome. Such partitioning of repeats, resulting in regions which are relatively rich or poor with respect to their IRE content, often leads to a non-uniform distribution of IRE PCR products, leaving some regions of the genome significantly under-represented.

The use of a bubble primer in PCR has also been reported. Such use, however, has been limited to use in conjunction with a second primer which is derived from a unique region of the source DNA whose sequence and specific location relative to the region desired to be amplified are known. This method is thus also limited in that only regions of the genome in which the sequence of a specific adjacent region is known, can be amplified.

SUMMARY OF THE INVENTION

It is an object of the invention to provide a rapid method for efficient and representative amplification of genomic DNA sequences from complex sources.

It is yet another object of the invention to generate a more complex and randomly distributed amplification product than previous methods.

It is yet another object of the invention to generate a unique set of short single copy sequences which are representative of any desired genomic DNA segment.

It is yet another object of the invention to amplify species-specific DNA of somatic cell hybrids, YACs, cosmids, phage, BACs, PACs and other recombinant vectors.

It is yet another object of the invention to provide an amplification method which does not require knowledge of individual specific genomic sequences adjacent to each of the regions that are desired to be amplified on the genome.

It is yet another object of the invention to provide a method for labeling the amplification products of the IRE-bubble PCR method of this invention for use in fluorescent in situ hybridization and chromosome painting.

It is yet another object of the invention to provide a method for easily and rapidly detecting the presence or absence of a chromosomal aberration in a nucleic acid.

It is yet another object of the invention to provide a method for easily and rapidly diagnosing a genetic disorder, cancer or other chromosome-related disease.

It is yet another object of the invention to generate a set of laddered markers for a particular chromosome for use in mapping unknown probes along that chromosome.

It is yet another object of the invention to rapidly generate clone libraries of significant complexity from specific, predetermined chromosomal or sub-chromosomal regions.

It is yet another object of the invention to generate sets of sequence tagged sites (STS) targeted to a particular chromosome or sub-chromosomal region.

Still another object of the invention is to provide a kit for generating IRE-bubble PCR products for a nucleic acid.

The present invention overcomes the limitations of previous PCR methods, resulting in enhanced ability to analyze various genomes. A simple, specific, amplification technique, called IRE-bubble PCR, is described. Using IRE-bubble PCR, virtually any DNA fragment which contains a single interspersed repetitive element can serve as a template for specific PCR amplification. For example, the IRE-bubble PCR amplification technique can result in substantially complete representation of the human DNA content of somatic cell hybrids, YACs, and cosmids.

According to the invention, a method for amplifying a nucleic acid fragment, called IRE-bubble PCR, is provided. A source nucleic acid, e.g, from a somatic cell hybrid, a YAC clone, a cosmid clone, a BAC clone, a plasmid clone or a phage clone, having interspersed repetitive elements, e.g., Alu, Line, O, MER, mouse B1 or mouse L1, is cleaved, e.g. with a blunt cutting restriction enzyme, so as to obtain nucleic acid fragments. A bubble oligonucleotide, having two double stranded portions, each preferably comprising approximately 10 to approximately 50 complementary nucleotides, flanking a substantially non-complementary portion consisting of a first and a second single strand, each preferably approximately 15 to approximately 35 nucleotides, is ligated to the nucleic acid fragments to make bubble/nucleic acid units having a first strand and a second strand.

The units are treated with a first oligonucleotide primer that is substantially complementary to at least a portion of the interspersed repetitive element on the first strand of the unit. Preferred primers include, e.g., sequences represented by Alu-S, Alu-J, Alu-end, 47-23, LIHS, MER1, MER2, MER4 through MER22, mouse B1Mv3CH and mouse B25'notl. The treatment is done under conditions such that an extension product of this primer is synthesized which is complementary to the first strand of the unit. The extension product contains a complementary region to at least a part of the first single strand of the bubble oligonucleotide.

The units are treated with a second oligonucleotide primer, preferably approximately 15 to approximately 35 nucleotides, that is substantially complementary to at least a portion of the extension product of the first primer, this portion of the extension product containing sequences complementary to the first single strand of the bubble oligonucleotide. Preferably, the second primer is able to hybridize to the complement of the first single strand of the non-complementary portion of the bubble oligonucleotide, but is not able to hybridize to the second strand of the non-complementary portion of the bubble oligonucleotide. This treatment with the second primer is done under conditions such that an extension product of the second primer is synthesized which is complementary to the extension product of the first primer. These conditions include, e.g., treating the units with four different nucleoside triphosphates and an agent for polymerization of the nucleoside triphosphates, e.g., a thermostabile polymerase. In one embodiment, the second primer has the sequence 5'-GCG-GCCGCAGTTCGTCAACATAGCATTTCT-3' (Seq. ID No. 7).

The primer extension products are separated from their complements to produce separated single stranded extension products. These single stranded extension products are treated with the first and second primers under conditions such that an extension product is synthesized from each of the single stranded extension products. These separations and treatments can be repeated.

The invention also provides for the product made in accordance with the above described method. In one embodiment, this product is treated with biotin, digoxigenin, fluorescein, or mixtures thereof, for use in cytogenetic analysis by fluorescence in situ hybridization.

The invention also features a bubble oligonucleotide whose first strand has the nucleotide sequence 5'CTCTC-CCTTCTGCGGCCGCAGTTCGTCAACATAGCATTTC TGTCCTCTCCTTC-3' (Seq. ID No. 5) and whose second strand has the nucleotide sequence 5'-GAAGGAGAG-GACGCTGTCTGTCGAAGGTA AACGGAC-GAGAGAAGGGAGAG-3' (Seq. ID No. 6).

A single stranded oligonucleotide primer for nucleic acid synthesis along a complementary template is also provided. The primer has a region the sequence of which is substantially identical to the sequence of at least a portion of the first single strand of the bubble oligonucleotide just described. In one embodiment, the primer has the sequence 5'-GCGGC-CGCAGTTCGTCAACATAGCATTTCT-3' (Seq. ID No. 7).

Another aspect of the invention features labeling target nucleic acids. Nucleic acid fragments are amplified in accordance with the IRE-bubble PCR method described above, so as to obtain a heterogenous mixture of nucleic acid fragments. The heterogeneous mixture of nucleic acid fragments is labeled, and these labeled nucleic acid fragments are contacted with the target nucleic acid under conditions such that hybridization occurs between the labeled nucleic acid fragments and the target nucleic acid. In certain embodiments, the target nucleic acid is chromosomal metaphase or interphase nucleic acid. Preferably, substantial portions of the heterogenous mixture of the nucleic acid fragments have nucleic acid base sequences that are substantially complementary to the target nucleic acid. The labeling can be, e.g., radioactive labeling, direct fluorescent labeling or indirect fluorescent labeling.

The invention also features a method for detecting the presence or absence of a chromosomal aberration, e.g., a translocation, a deletion, an inversion, an amplification or an insertion, in a nucleic acid of a test organism. Nucleic acids, e.g., from somatic cells, germ line cells, a tissue, fetal cells, malignant cells, or amniotic fluid, of a test organism and a reference organism, are stained in accordance with the method described above, so as to produce a pattern of staining of the nucleic acids from each of the organisms. The staining patterns from the test organism and reference organism are compared so as to determine the presence or absence of different staining patterns between them. The presence or absence of the chromosomal aberration is determined based upon the presence or absence of the different staining patterns. Preferably, the chromosomal aberration is diagnostic for a genetic disorder, a predisposition to a genetic disorder, a malignant state of a cell, or a predisposition to a malignant state of a cell.

In addition, a kit for generating IRE-bubble PCR products from a target nucleic acid, is also provided. The kit is a multicontainer unit having a bubble oligonucleotide, a bubble primer, an interspersed repetitive element primer, each of four different nucleoside triphosphates, an agent for polymerization of the nucleoside triphosphates, and instructions regarding the use of the kit for generating IRE-bubble PCR products. In certain embodiments, the kit can also contain a restriction enzyme for cleaving the target nucleic acid, and/or a T-vector and ligase for cloning of the generated IRE-bubble PCR products.

The above and other objects, features and advantages of the present invention will be better understood from the following specification when read in conjunction with the accompanying drawings.

DETAILED DESCRIPTION

Figure 1:
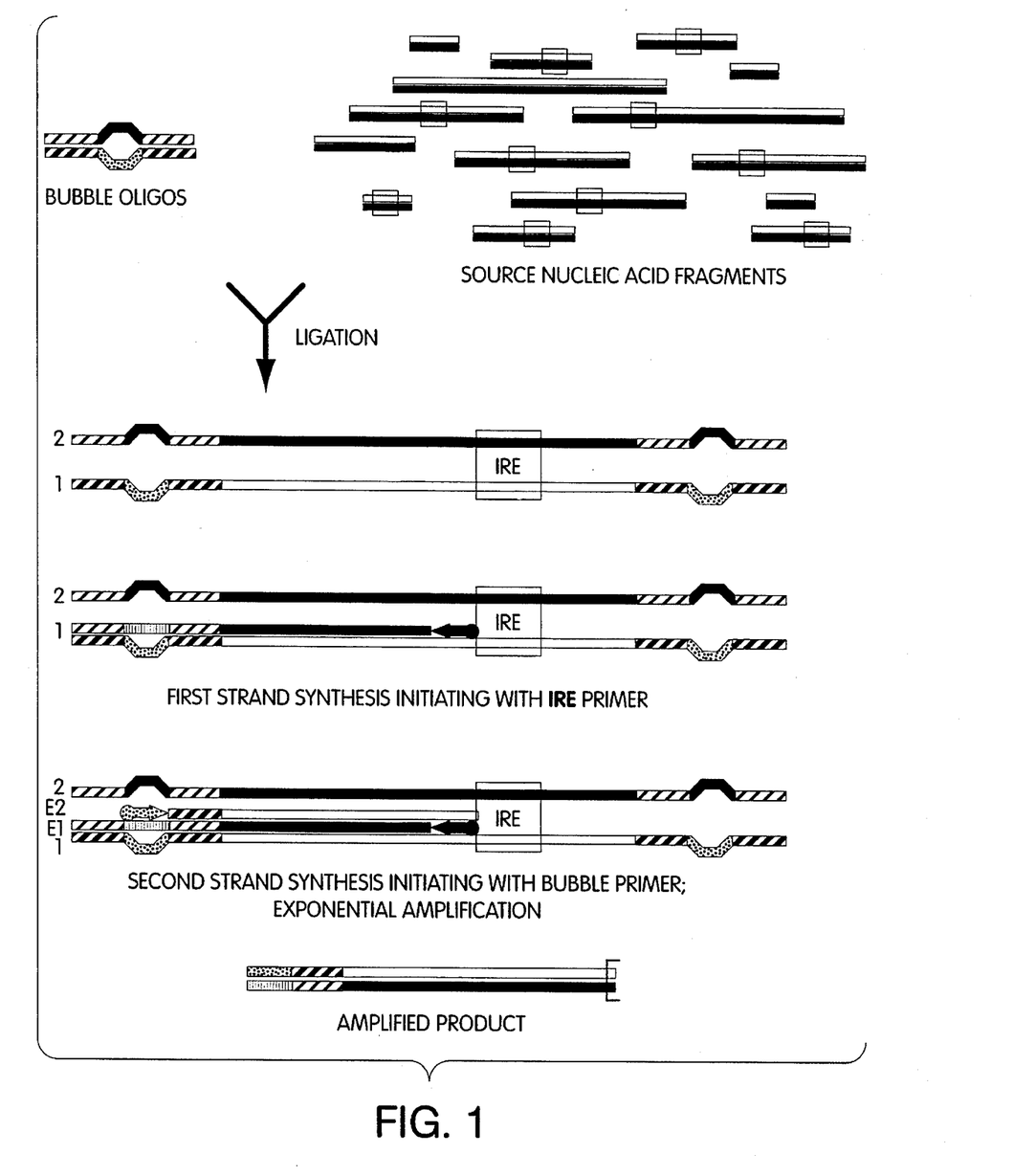
FIG. 1 depicts a schematic representation of the IRE-bubble PCR amplification method of this invention.

This invention provides a method for amplifying a nucleic acid fragment. A preferred embodiment is schematically shown in FIG. 1. A source nucleic acid having interspersed repetitive elements (IREs) is cleaved so as to obtain nucleic acid fragments. A bubble oligonucleotide, having two double stranded portions flanking a substantially non-complementary portion consisting of a first and a second single strand, is ligated to the nucleic acid fragments to make bubble/nucleic acid units having a first strand (denoted "1" in FIG. 1) and a second strand (denoted "2" in FIG. 1).

The units are treated with a first primer that is substantially complementary to at least a portion of the interspersed repetitive element on the first strand of the unit under conditions such that an extension product (denoted "E1" in FIG. 1) of this primer is synthesized which is complementary to the first strand of the unit. The extension product contains a complementary region to at least a part of the first single strand of the bubble oligonucleotide.

The units are treated with a second primer that is substantially complementary to at least a portion of the extension product of the first primer, this portion of the extension product containing sequences complementary to the first single strand of the bubble oligonucleotide. This treatment is done under conditions such that an extension product (denoted "E2" in FIG. 1) of the second primer is synthesized which is complementary to the extension product of the first primer.

The extension products are separated from their complements to produce separated single stranded extension products. These single stranded extension products are treated with the first and second primers under conditions such that an extension product is synthesized from each of the single stranded extension products. Preferably, these separations and treatments are repeated at least once, and more preferably they are repeated 25–40 times.

The source nucleic acid can be any nucleic acid for which amplification is desired. The method is particularly useful for amplifying nucleic acids having a high degree of complexity and in which the sequence is substantially unknown. The source nucleic acid can be, e.g., genomic or recombinant nucleic acids. It includes nucleic acids derived from, e.g., somatic or germ line cells, tissues, fetal cells, malignant cells or amniotic fluid. It can be from, e.g., a somatic cell hybrid, a YAC clone, a cosmid clone, a BAC clone, a PAC clone, a plasmid clone, a phage clone or other recombinant vector clone. By somatic cell hybrid is meant the fusion of cells from different species, e.g., between human cells and rodent cells. Such somatic cell hybrids are particularly useful in this invention for amplification of human DNA of unknown sequence. By YAC is meant yeast artificial chromosome. By BAC is meant bacterial artificial chromosome. By PAC is meant P1 artificial chromosome.

The source nucleic acid must have interspersed repetitive elements. By interspersed repetitive element is meant sequences that are present in more than one copy in the genome and that are dispersed about the genome. Interspersed repetitive elements are meant to include families of sequences that are the same, as well as those that are not exactly the same, but are sufficiently similar so as to be able to renature with each other. Preferably, the interspersed repetitive element is present in at least approximately 10,000 copies per haploid genome, and more preferably is present in approximately 100,000 to approximately 1,000,000 copies per haploid genome. Examples of interspersed repetitive elements are Alu, Line, O and MER. Alu is approximately 300 base pairs long and is present in the human genome at approximately 900,000 copies per haploid genome, giving an average distance between copies of about 4 kilobases. This distance, however, apparently varies considerably, since Alu sequences appear to be enriched in certain chromosomal regions and deficient in other regions.

Figure 2:
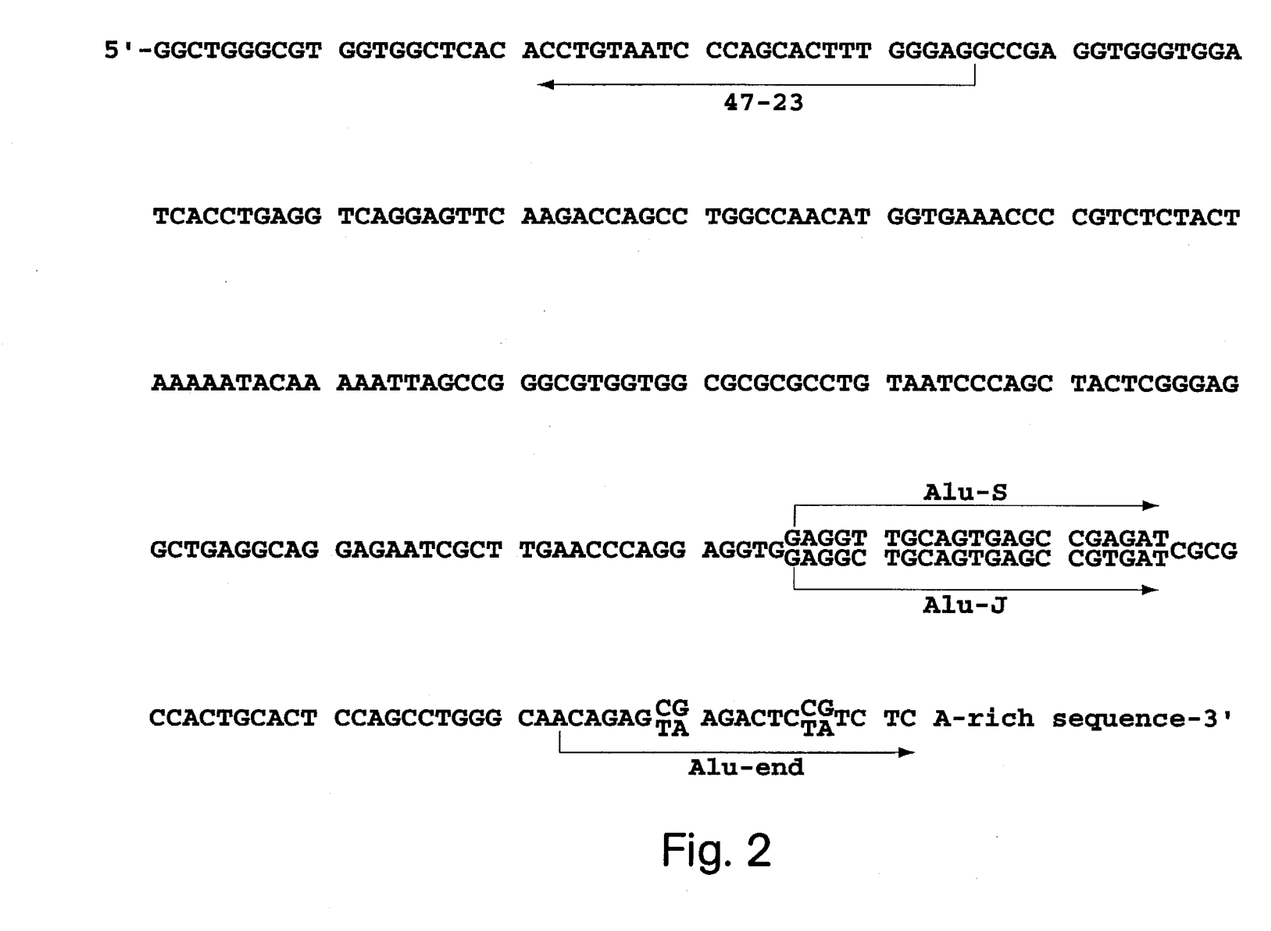
FIG. 2 depicts the consensus Alu sequence (Seq. ID No. 8) and the location of the 47-23 (Seq. ID No. 1), Alu-S (Seq. ID No. 2), Alu-J (Seq. ID No. 3) and Alu-end (Seq. ID No. 4) regions used as primers.

FIG. 2 shows the consensus sequence of the Alu repeat element (Seq. ID No. 8) (Schmid and Jelinke, Science 216: 1065–1070, 1982; Jurka and Smith, Proc. Nat'l Acad. Sci., USA 85: 4775–4778, 1988; Bains, J. Mol. Evol. 23: 189–199, 1986; Batzer et al., Nucl. Acid Res. 18: 6793–6798, 1990). The location and orientation of examples of regions of Alu which can be used as primers in this invention, e.g., 47-23, Alu-S, Alu-J and Alu-end, are indicated by arrows. 47-23 has the sequence: 5'-GAGGGTTTCACGACCCTAATGT CC-3' (Seq. ID No. 1). Alu-S has the sequence: 5'-GAGGTTGCAGTGAGC-CGAGAT-3' (Seq. ID No. 2). Alu-J has the sequence 5'-GAGGCTGCAGTGAGCCGTGAT-3' (Seq. ID No. 3). Alu-end has the sequence: 5'-ACAGAG(C/T)(G/A) AGACTC(C/T)(G/A)TCTC-3' (Seq. ID No. 4).

L1HS is a region in the Line repeat element, and is present in the human genome as a complete or truncated approximately 6.4 kilobase sequence with approximately 10,000 to approximately 100,000 copies per haploid genome. Some of the O repeats are approximately 270 base pairs to approximately 420 base pairs long. O is present in the human genome at approximately 10,000 to approximately 100,000 copies per haploid genome. Each of at least 21MER sequences within the MER family are found in the human genome at aprproximately 200 to 10,000 copies per haploid genome, and are approximately 150 base pairs to 650 base pairs long.

AlU and L1HS interspersed repetitive elements are also found in rodent genomes. However, there is sufficient sequence divergence to significantly reduce cross hybridization between human and rodent Alu or L1HS sequences. This divergence permits the use in this invention of certain regions in these elements as human specific primers, e.g., when the source DNA is human-mouse somatic cell hybrids and it is desired to amplify only the human DNA sequences. Examples of human specific regions in interspersed repetitive elements are Alu-S, Alu-J, Alu-end, L1HS, MER1, MER2 and MER 4 through MER 22. Species-specific amplification can also be applied to species other than humans. For example, species specific primers corresponding to conserved regions of, e.g., the mouse L1, e.g., B1Mv3CH, and B2, e.g., B25'notl, repetitive elements, can be used for generating mouse-specific IRE-bubble PCR products from, e.g., mouse-hamster somatic cell hybrids.

By cleaving the source nucleic acid is meant cutting the nucleic acid strands. Cleaving can be accomplished, e.g., by cutting with a restriction enzyme or by mechanically shearing the nucleic acid. Restriction enzymes refer to bacterial enzymes, each of which cuts double-stranded DNA at or near a specific nucleotide sequence. Restriction enzymes result in nucleic acids with blunt ends or staggered ends. Preferred restriction enzymes are blunt cutting restriction enzymes with a 4 base recognition sequence, e.g., AluI, RsaI or HaeIII. These enzymes generally produce average size fragments in the 300 to 1000 base pair range. Preferably, the restriction enzymes is heat inactivatable.

The bubble oligonucleotide of the invention has a substantially non-complementary portion consisting of two single strands. These two single strands can be the same or of different lengths with respect to each other. The single strands must be long enough so that a primer can hybridize to the complement of one of the single strands with enough specificity so as to effectively result in a polymerase chain reaction. This length is about 5 nucleotides. While there is no absolute upper limit to the length of the single strands, the longer the length, the greater the chance of random sequences between the two strands or between the primer and one of the strands base pairing with each other. Preferably, the length of each of the two single stranded regions is approximately 15 nucleotides to approximately 35 nucleotides.

The two single strands have different sequences with respect to each other. The difference in sequence is such that the second primer, described below, hybridizes to the complement of the first strand of the bubble oligonucleotide, but does not hybridize to the second strand of the bubble oligonucleotide, under the conditions of the polymerase chain reaction of this invention.

The two single strands just described are flanked on each side by double stranded regions. The double stranded regions are each preferably approximately 10 to approximately 50 nucleotides long.

Figure 3:
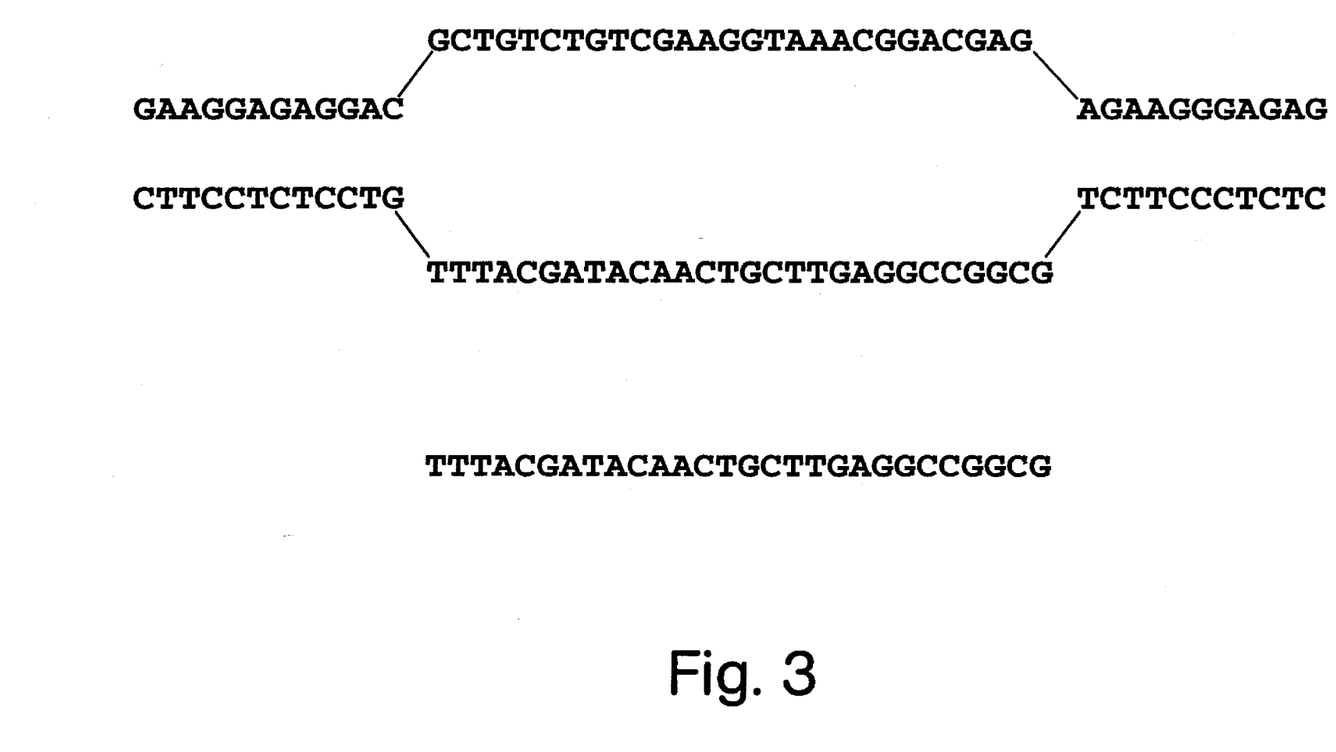
FIG. 3 depicts the sequence of a preferred bubble oligonucleotide (Seq. ID No. 5; Seq. ID No. 6) and a preferred second primer (Seq. ID No. 7) of this invention.

A preferred sequence for the first strand of the bubble oligonucleotide (which includes both the non-complementary single stranded bases and the complementary bases that will be part of the two double stranded regions when they hybridize to their complements), is: 5'-CTCTCCCTTCT-GCGGCCGCAGTTCGTCAA CATAGCATTTCTGTC-CTCTCCTTC-3' (Seq. ID No. 5). A preferred sequence for the second strand of the bubble oligonucleotide (which includes both the non-complementary single stranded bases and the complementary bases that will be part of the two double stranded regions when they hybridize to their complements) is: 5'-GAAGGAGAGGACGCTGTCTGTC-GAAGGTAA ACGGACGAGAGAAGGGAGAG-3' (Seq. ID No. 6). The top of FIG. 3 shows the sequence of a preferred bubble oligonucleotide formed by annealing the two strands just described.

Ligation occurs between the ends of the double stranded regions of the bubble oligonucleotide and the nucleic acid fragments described above, to make bubble/nucleic acid units.

By primer is meant an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of appropriate nucleoside triphosphates and an agent for polymerization in an appropriate buffer ("buffer" includes pH, ionic strength and cofactors) and at a suitable temperature. The primer must be sufficiently long to prime the synthesis of extension products in the presence of the agent for polymerization. The exact lengths of the primers will depend on many factors, including temperature, source of primer, complexity of target sequence and use of the method. Primers will typically contain 15–35 nucleotides, although they may contain more or fewer nucleotides. Short primer molecules generally require lower temperatures to form sufficiently stable hybrid complexes with the template.

The two oligonucleotide primers used are a first primer, denoted the interspersed repetitive element primer, and a second primer, denoted the bubble primer. Preferably, these primers are obtained by automated synthesis. The use of these primers in this invention ensures that first strand synthesis is initiated with the interspersed repetitive element primer and not the bubble primer. The bubble primer is not complementary to either of the two single stranded regions of the bubble oligonucleotide, but rather, is substantially complementary to the complement of one of the single stranded regions. Therefore, first strand synthesis cannot be initiated with the bubble primer. First strand synthesis is initiated with the second primer which is complementary to a portion of the interspersed repetitive element present in the source nucleic acid. The extension product which results from this first strand synthesis contains sequences which are complementary to the bubble primer, thus permitting the bubble primer to prime this first extension product and produce an extension product complementary to the first extension product. This polymerase chain reaction scheme thus enables amplification of species specific sequences from source DNA which contains DNA from more than one species, e.g., of human sequences which are derived from human-mouse somatic cell hybrids, simply by choosing the first primer to be complementary to a region of an interspersed repetitive element that is present in one of the species and not the other.

The choice of the first primer, the interspersed repetitive element primer, depends upon the species of the source DNA that is desired to be amplified. The interspersed repetitive element primer must be at least partially complementary to an interspersed repetitive element e.g., Alu, Line, O, MER, mouse B1 or mouse L1, that is present in the source DNA. Examples include primers having sequences represented by the subregions Alu-S, Alu-J, Alu-end, 47-23, L1HS, MER1, MER2, MER4 through MER22, B1Mv3CH and B25'notl. Primers which correspond to parts of the sequences represented by the above subregions can also be used.

In situations where the source DNA contains DNA from more than one species, it is preferable that the primer be at least partially complementary to a species specific region of the interspersed repetitive element. Preferred human specific first primers are oligonucleotides which have sequences represented by Alu-S, Alu-J, Alu-end, L1HS, MER1, MER2, and MER4 through MER 22. Preferred mouse specific first primers are oligonucleotides which have sequences represented by mouse L1, e.g., B1Mv3CH, and mouse B2, e.g., B25'notl.

In certain embodiments, first primers from a second repeat family can be used to increase the distribution of products from areas of the genome that prove to be underrepresented for the first repeat family used. For example, L1HS can be used for Alu "poor" regions.

The second primer, the bubble primer, is not able to hybridize to either the first or second strand of the non-complementary portion of the bubble oligonucleotide, but is able to hybridize to the complement of the first strand of the non-complementary portion of the bubble oligonucleotide, under the hybridization conditions used in the PCR method of this invention. This primer can hybridize to the entire region or to only a portion of the first strand of the non-complementary portion of the bubble oligonucleotide. Preferably, the length of the primer is approximately 15 nucleotides to approximately 35 nucleotides. In a preferred embodiment, the second primer has the sequence: 5'-GCG-GCCGCAGTTCGTCAACATAGCATTTCT-3' (Seq. ID No. 7), as shown in the bottom of FIG. 3.

The IRE-bubble PCR method of this invention generates a more complex and randomly distributed amplification product than previous methods which use interspersed repetitive element primers for both the first and second primers. Because this invention uses only one interspersed repetitive element primer, the extension products that are made are not dependent upon there being two interspersed repetitive elements within a short enough distance and in the proper orientation for amplification to occur. Thus, regions of a genome which are poorly represented for a given interspersed repetitive element, show enhanced amplification with the method of this invention as compared to prior methods which require two interspersed repetitive element primers.

The IRE-bubble PCR method is also more versatile as compared to previous methods which use a bubble primer because in these previous methods the other primer is derived from a unique region of the source DNA whose sequence and location relative to the region desired to be amplified must be known. The method of this invention does not require knowledge of individual specific genomic sequences adjacent to each of the regions that are desired to be amplified on the genome. Rather, it relies only on knowing the sequence of one interspersed repetitive element region that is to be used as the complement to the primer, which is ubiquitous throughout the genome. The method of this invention, therefore is much less restrictive and more versatile.

The conditions required for the IRE-bubble PCR to occur include treating the bubble/nucleic acid units with four different nucleoside triphosphates, e.g., dTTP, dATP, dGTP and dCTP, and an agent for polymerization of the nucleoside triphosphates. The agent for polymerization may be any compound, e.g., an enzyme, which will function to accomplish the synthesis of primer extension products. Preferably, the agent is a thermostabile polymerase, e.g., *Thermus aquaticus* polymerase. In a preferred embodiment, the specificity and efficiency of amplification is maximized by using a "hot-start" procedure which involves separately heating one or more of the PCR ingredients from the rest of the reaction components. The two separate sets of components are mixed only after they reach the denaturation temperature so as to prevent promiscuous priming which may occur as the temperature is elevated to the denaturation temperature for the initial denaturation.

The invention also includes amplifying at least one nucleic acid fragment derived from a source nucleic acid having an interspersed repetitive element. At least one bubble/oligonucleotide unit having a first stand and a second strand is provided. The unit has at least one nucleic acid fragment and at least one bubble oligonucleotide having a first and a second double stranded portion. Each of the double stranded portions flank a substantially non-complementary portion consisting of a first single strand and a second single strand. At least one unit is treated with a first oligonucleotide primer that is substantially complementary to at least a portion of the interspersed repetitive element on the first strand of the unit under conditions such that an extension product of the first primer is synthesized which is complementary to the first strand of the unit. The extension product contains a complementary region to at least a part of the first single strand of the bubble oligonucleotide. At least one unit is treated with a second oligonucleotide primer that is substantially complementary to at least a portion of the extension product of the first primer. The portion of the extension product of the first primer contains sequences complementary to the part of the first single strand of the bubble oligonucleotide. The treatment is done under conditions such that an extension product of the second primer is synthesized which is complementary to the extension product of the first primer.

The complexity and representation of the product generated by the IRE-bubble PCR method of this invention makes it especially useful for many applications. Uses of this invention include fluorescent in situ hybridization (FISH) mapping and chromosome painting. For example, using available monochromosomal somatic cell hybrids or sets of reduced somatic cell hybrids, a probe recognizing the entire length or a defined fraction of each individual chromosome of the different species' chromosomes can be produced. These probes are useful as diagnostic aids for detecting chromosomal aberrations associated with specific genetic disorders, cancers or other diseases. Moreover, the nucleic acid content and integrity of any somatic cell hybrid, YAC, cosmid, phage, BAC or other recombinant vector, can be quickly assessed. In addition, probes derived from, e.g., YACs or YAC contigs, which map at defined intervals along a specific chromosome can be used to generate a quick and easy set of laddered markers for that particular chromosome which will allow precise mapping of an unknown probe along that chromosome. The generated products of this invention are also useful as radioactive probes.

The diversity of products resulting from the IRE-bubble PCR of this invention has utility for rapidly generating clone libraries of significant complexity from specific, pre-determined chromosomal or sub-chromosomal regions. Cloned IRE-bubble PCR products are also useful following sequencing for the generation of sets of sequence tagged sites (STS) targeted to a particular chromosome or sub-chromosomal region.

This invention includes the amplification product made in accordance with the method described above. In certain embodiments, this product is treated with a compound, e.g., biotin, digoxigenin, fluorescein or mixtures thereof. Such a treated product can be used, e.g., for cytogenetic analysis by fluorescent in situ hybridization. Radioactive hybridization probes can also be made.

This invention also includes the bubble oligonucleotide as shown in the top of FIG. 3.

A primer for nucleic acid synthesis along a complementary strand, the primer being a single stranded oligonucleotide having a region whose sequence is substantially identical to the sequence of at least a portion of the first single strand of the bubble oligonucleotide of this invention, is also part of this invention. In a preferred embodiment, the primer has the sequence: 5'-GCGGCCGCAGTTCGTCAAC ATAGCATTTCT-3' (Seq. ID No. 7).

In methods of the invention, target nucleic acids are labeled. Nucleic acid fragments are amplified in accordance with the IRE-bubble PCR method described above, so as to obtain a heterogenous mixture of nucleic acid fragments, the heterogenous mixture of nucleic acid fragments are labeled, and these labeled nucleic acid fragments are contacted with the target nucleic acid under conditions such that hybridization occurs between the labeled nucleic acid fragments and the target nucleic acid. In certain embodiments, the target nucleic acid is chromosomal metaphase or interphase nucleic acid. Preferably, substantial portions of the heterogenous mixture of the nucleic acid fragments have nucleic acid base sequences that are substantially complementary to the target nucleic acid. By labeling nucleic acids is meant any procedure which results in some type of tagged nucleic acid which can be identified. The labeling can be, e.g., radioactive labeling, direct fluorescent labeling or indirect fluorescent labeling.

Direct fluorescent labeling involves the direct incorporation of 2'-dNTP-5'triphosphate coupled to fluorescein via a spacer arm. The fluorescent dNTP analog can be incorporated, e.g., by standard nick-translation, random primed labeling, reverse transcriptase reactions or terminal transferase reactions. Examples of such compounds include fluorescein-12-dUTP (12 atom spacer) and fluorescein-16-dCTP. Alternatively, 2'3'dideoxyNTP-5'triphosphates coupled to fluorescein via a spacer arm can be used to directly 3'-end label probes with DNA polymerase, e.g., fluorescein-12-ddUTP.

Indirect fluorescent labeling involves the incorporation of 2'-dNTP-5'triphosphate coupled to fluorescein, biotin, or digoxigenin via a spacer arm. As in direct labeling procedures, these compounds can be incorporated into probe by, e.g., standard nick-translation, random primed labeling, reverse transcriptase reactions, or terminal transferase reactions. Examples of such compounds include fluorescein-12-dUTP, biotin-21-dUTP, biotin-14-dCTP, and digoxigenin-11-dUTP. Mixtures of these compounds can also be used. Probes labeled with biotin coupled reagents can be detected with streptaviden conjugated flurochromes such as aviden-fluorescein isothiocynates. Probes labeled with fluorescein or digoxigenin coupled reagents can be detected with an anti-fluorescein antibody conjugated fluorochrome or an anti-digoxigenin antibody conjugated fluorochrome, respectively. Examples of such compounds include goat-anti-digoxigenin conjugated fluorescein. The signals obtained with probes detected by aviden-fluorescein conjugates can be enhanced by subsequent probing with anti-aviden antibody conjugated fluorochromes. The fluorochromes can be, e.g., yellow, green, or orange (e.g., fluorescein or the Spectrum Green and Spectrum Orange fluorophores manufactured by Imagenetics of Framingham, Mass. Antibodies can also be conjugated to the fluorescent dye, TexasRed. Additional colors are available by appropriate mixing of the commonly available fluorochromes.

If labeling is performed for fluorescent staining, hybridization preferably is fluorescence in situ hybridization. In certain embodiments the target nucleic acid is chromosomal metaphase or interphase nucleic acid. When fluorescence in situ hybridization is performed, preferably the nucleic acid is metaphase nucleic acid. The fluorescence in situ hybridization gives a particular staining pattern for the particular target nucleic acid used.

In one embodiment of the invention, a method for detecting the presence or absence of a chromosomal aberration in a nucleic acid of a test organism is also provided. Nucleic acids from a test organism and from a reference organism are stained in accordance with the method described above, so as to produce a pattern of staining of the nucleic acids from each of the organisms. The staining patterns from the test organism and reference organism are compared so as to determine the presence or absence of different staining patterns between them. The presence or absence of the chromosomal aberration is determined based upon the presence or absence of the different staining patterns.

The nucleic acid can be derived from, e.g., somatic cells, germ line cells, a tissue, fetal cells malignant cells, or amniotic fluid.

Chromosomal aberrations include, e.g., duplicated chromosomes, missing chromosomes, duplicated portions of chromosomes, missing portions of chromosomes, breaks, rings, dicentrics and chromosomal rearrangements. Chromosomal rearrangements include, e.g., translocations, deletions, inversions, amplifications and insertions.

By reference organism is meant an organism that does not contain the chromosomal aberration under investigation. By test organism is meant an organism which is to be tested for the presence or absence of a chromosomal aberration. In preferred embodiments, the staining of the nucleic acids is achieved by treating with a compound, e.g., biotin, digoxigenin, fluorescein or mixtures thereof, as described above, and fluorescence in situ hybridization is performed. A pattern of staining results from this fluorescent labeling.

Comparisons of the staining patterns produced from the test organism and the reference organism can indicate the presence or absence of a chromosomal aberration. The presence of a chromosomal aberration can be diagnostic for a genetic disorder or for a predisposition to a genetic disorder, or for a malignant state of a cell or for a predisposition to a malignant state of a cell. The present invention can also be used to detect chromosomal aberrations that are responsible for a desirable characteristic.

Genetic disorders associated with chromosomal aberrations include, e.g., fragile X syndrome, WAGR syndrome, Ataxia telangiectasia, DiGeorge syndrome, Turner's syndrome, Klinefelter's syndome, Cri du Chat syndrome, Down's syndrome, Duchenne Muscular Dystrophy (DMD) and myleodesplasia. Malignancies associated with chromosomal aberrations include, e.g., lymphomas, T-cell leukemias, acute myelocytic leukemia (AML), and solid tumors.

Examples of lymphomas include Burkett's lymphoma associated with t(8;14) (chromosome 8 to chromosome 14 translocation), t(2;8), and t(8;22); KI-1 associated with t(5;8); CLL and ILL associated with t(11;14); CML associated with t(9;22) or Philadelphia chromosome or a del(22) (chromosome 22 deletion); and low grade lymphomas associated with t(14;18). T-cell leukemias are commonly associated with t(7;14), t(10;14), t(7;9), or inv(14) (chromosome 14 inversion). AML is commonly associated with trisomy 8, monosomy 7, t(15;17), t(8;21), or translocations involving chromosome 3 or chromosome 11q23, and inv(16) and inv(3). Examples of solid tumors include sinovial cell sarcoma associated with t(X;18); Ewing's sarcoma associated with t(11;22); renal cell carcinoma associated with t(3;8) and del(3); melanomas associated with del(9); small cell lung cancer associated with del(3); retina blastoma associated with del(13); rhabdomyosarcoma associated with chromosome 11 translocation or del(11); and rhabdoid tumors associated with chromosome 2 translocations.

This invention further provides a kit for generating IRE-bubble PCR products from a target nucleic acid, which has in packaged form a multicontainer unit having a bubble oligonucleotide as described above; a bubble primer whose nucleotide sequence is able to hybridize to the complement of the first strand, but not the second strand, of the non-complementary portion of the bubble oligonucleotide; an interspersed repetitive element primer whose nucleotide sequence is substantially complementary to at least a portion of an interspersed repetitive element that is present in the target nucleic acid; each of four different nucleoside triphosphates; and an agent for polymerization of the nucleoside triphosphates. Instructions providing information to the user regarding the use of the kit for generating IRE-bubble PCR products can also be included. In one embodiment the kit also has a restriction enzyme for cleaving the target nucleic acid fragments for ligation to the bubble oligonucleotide. In another embodiment the kit also has a T-vector and ligase, preferably T4 DNA ligase, for cloning of the generated IRE-bubble PCR products. Frozen competent bacteria may also be included. The kit can comprise a rectangular cardboard box containing sealed glass or plastic vials carrying each of the components of the kit with or without a suitable printed instruction sheet.

EXAMPLES

Example 1—Preparation of Annealed Bubble Oligonucleotides

This example illustrates preparation of annealed bubble oligonucleotides from single strands. Bubble oligonucleotides were annealed in a total volume of 333 µl with each of the single strands (obtained by automated synthesis) at 3 pM/µl, in 2X SSC (17.5 gm NaCl, 8.82 gm Na-citrate/liter)/10 mM Tris (pH 8.0). The annealing cocktail was boiled for 10 minutes and slowly cooled to ambient temperature.

Example 2—Construction of Bubble/Nucleic Acid Units

This example illustrates construction of bubble/nucleic acid units from genomic DNA and bubble oligonucleotides. 0.5 µg of genomic DNA was digested to completion with a restriction enzyme in a total volume of 120 µl according to the restriction enzyme manufacturer's specifications. Following the digestion reaction, the restriction enzyme was heat-inactivated for 20 minutes at 65° C. 0.25 µg of digested genomic DNA (60 µl) was ligated with 12 pM of annealed bubble oligonucleotides described in Example 1, in a 100 µl reaction at ambient temperature for 12–18 hours. The ligation reaction was then diluted to 1.5 ng/μl with ¼X TE (2.5 mM Tris (pH 8.0), 0.25 mM EDTA). The ligase was then heat-inactivated by incubating at 65° C. for 10 minutes.

Example 3—IRE-Bubble PCR Amplification

This example illustrates one embodiment of the IRE-bubble PCR amplification procedure. IRE-bubble PCR was carried out using a "hot-start" procedure in a total reaction volume of 50 μl consisting of 1N5-7N5 ng of template, 1 μM of the IRE primer, 1 μM of the bubble primer, and 2.5 units of *Thermus aquaticus* (Taq) polymerase in 50 mM KCl/10 mM Tris, pH 8.0)/1.5 mMMgCl$_2$/0.01% gelatin/0.05% NP40/300 μM dATP, dCTP, dGTP, dTTP, with the following cycling times: 94° C. for 3 minutes followed by 30 cycles of 94° C. for 15 seconds, 63° C. for 10 seconds and 72° C. for 1.5 minutes followed by 72° C. for 5 minutes. PCR from YAC, cosmid or phage templates was carried out with a 59° C./45 second annealing cycle.

Inter-Alu PCR was carried out under identical conditions using 25 ng of genomic DNA template.

Example 4—T-vector Preparation for Direct Cloning of IRE-Bubble PCR Products

This example illustrates preparation of T-vectors used for direct cloning of IRE-bubble PCR products. Direct cloning of PCR products is usually somewhat difficult. Presumably, this is a consequence of "ragged" ends on DNAs synthesized by Taq polymerase. These "ragged" ends arise by virtue of the tendency of Taq polymerase to add a single non-template-directed residue to the 3' end of duplex PCR products. Usually this extra residue is a deoxyadenosine (A). T-vectors contain a single 3'-overhanging T-residue which lacks a 3'-hydroxyl (OH). Such vectors, while unable to self ligate, are capable of forming a phosphodiester bond with a PCR product that contains a single overhanging A. T-vectors are constructed simply by incubating linearized, blunt-ended plasmid vector in the presence of Taq polymerase and dTTP.

T-vector was prepared essentially as described by Marchuck et al., Nucl. Acid Res. 19:1154, 1990. 3 μg of pBluescript KS$^+$ was digested to completion with EcoRV according to the manufacturer's specifications. Digestion products were extracted 2× with phenol:CHCl$_3$:isoamyl alcohol (25:24:1), 1× with CHCl$_3$, ethanol precipitated, resuspended in 146 μl ddH$_2$O, 20μl 10× PCR buffer (as described in Example 3), 32 μl 11.25 mM dTTP, and 5 units of Taq polymerase, and incubated for 2 hours at 75° C. The reaction volume was then brought up to 400 μl with ¼× TE (2.5 mM Tris (pH 8.0), 0.25 mM EDTA), extracted 1× with phenol:CHCl$_3$:isoamyl alcohol (25:24:1), 1× with CHCl$_3$, ethanol precipitated, and resuspended in 100 μl¼ × TE. 50 ng aliquots were lyophilized and stored at −20° C.

Cloning into the T-vector was accomplished by standard methods. The ligation reaction (10 μl final volume) had 50 ng T-vector, 100–200 ng of the IRE-bubble PCR product to be inserted, 1 unit T4 DNA ligase, 1 μl 10X T4 DNA ligase buffer (200 mM Tris (pH 7.6), 100 mM MgCl$_2$, 100 mM DTT, 10 mM ATP).

Example 5—DNA Probe Preparation From IRE-Bubble PCR Products

This example illustrates preparation of DNA probes from IRE-bubble PCR products. Following IRE-bubble PCR amplification as described in Example 3, equal volumes of each individual reaction, specific to a given genomic DNA segment, were mixed and "blunt-ended" in a 200 μl reaction consisting of 0.1M MgAc, 0.5 mM dithiothreitol, 0.125 mM dNTP, 1 mg/ml BSA, 20 μm ATP, 9 units T4 DNA polymerase, and 10 units T4 DNA kinase. Following a 30 minute incubation at 37° C. the reaction volume was adjusted to 400 μl with ¼× TE, extracted 1× with phenol:CHCl$_3$:isoamyl alcohol (25:24:1), 1× with CHCl$_3$, ethanol precipitated, and ligated in a 125 μl reaction volume at ambient temperature for 12–18 hours. These concatamerized PCR products were used for labeling by nick-translation or random priming.

Example 6—Fluorescence In Situ Hybridization

This example illustrates a procedure for fluorescence in situ hybridization (FISH). (Lichter et al., Proc. Nat'l Acad. Sci. USA, 87: 6634–6638, 1990). Metaphase spreads were obtained from peripheral blood lymphocytes of a healthy donor and cultured following methotrexate synchronization and bromodeoxyuridine (BrdU) incorporation as described by Cherif et al., Proc. Nat'l Acad. Sci. USA, 87:6639–6643, 1990. BrdU incorporation permitted chromosomal identification and probe localization on the basis of R banding. Briefly, after culturing peripheral blood lymphocytes for 72 hours at 37° C., methotrexate ($10^{-5}$M) was added for 17 hours. The methotrexate was then washed off with RPMI 1640 and the cells were resuspended in RPMI 1640 with 20% serum and BrdU (0.1M). After incubation for 5 hours at 37° C., colcimid (0.06 μg/ml) was added for 7 minutes and the cell suspension subjected to centrifugation immediately. The supernatant was removed and the cells placed in a hypotonic solution of 0.075M KCl. After 20 minutes incubation at 37° C. the cells were fixed by a conventional methanol-acetic acid procedure and metaphase spreads were prepared.

Hybridization was performed following standard protocols (Lichter et al., Proc. Nat'l Acad. Sci. USA, 87: 6634–6638, 1990), with the exception of a photolysis step by a UV-Mercury lamp as described below. DNA (60 ng) was labeled with biotin-11-dUTP and precipitated with 3 μg of Cot 1DNA and 6 μg of salmon sperm DNA. The DNA mixture was resuspended in 10 μl of hybridization solution (50% formamide, 2× SSC, 10% dextran sulfate) and denatured at 76° C. for 10 minutes. The probe DNA was applied to the chromosome preparations which were denatured separately (2 minutes at 70° C., followed by dehydration through an ethanol series). A coverslip (18×18 mm$^2$) was added and sealed with rubber cement. Hybridization took place overnight at 37° C. After three 5 minute washes in 50% formamide, 2× SSC at 42° C., and three washes in 0.1× SSC at 60° C., non-specific background was blocked using 3% bovine serum albumin in 4× SSC. The slides were then stained with Hoechst 33258 (2.5 mg/ml) for fifteen minutes and briefly washed in distilled water. Metaphases were exposed to the light of a UV-mercury lamp at a distance of 10 cm for 1 hour, and then incubated in 2× SSC at 42° C. for an additional hour.

The probe sequences were then detected with aviden-DCS-Fluorescein isothiocyanate (obtained from Boehringer Maunheim Corp. of Indianapolis, Ind. The aviden-fluorophore conjugate was applied to the slide in 1% BSA and 4× SSC for 30 minutes at 37° C. After three washes in 4× SSC, 1% Tween at 42° C., the specimens were embedded in antifade (DABCO) containing propidium iodide (200 ng/ml) as a counterstain.

The fluorescent signals were visualized using a cooled CCD camera (PM512, obtained from Photometrics of Tucson, Ariz.). Gray scale images were obtained sequentially for fluorescein and propidium iodide with precision filter sets, manufactured by C. Zeiss, Germany, to minimize image shifts. Using custom computer software, the gray scale images were pseudo colored and merged. Photographs were taken using Kodak 100 HC color slide films and the fluorescent regions of the chromosomes were observed.

Example 7—Species Specificity of IRE-bubble PCR

This example illustrates the species specificity of IRE-bubble PCR. IRE-bubble PCR was performed on DNA from hamster genomic or human/hamster somatic cell hybrids whose human DNA content ranged from 5 megabases to an entire chromosome. (Cell lines described in Glaser et al., Somatic Cell and Mol. Gen., 15: 477–501, 1989; Jackson et al., Somatic Cell and Mol. Gen. 18:285–301, 1992). (See Table 1).

TABLE 1

Human DNA Content of Somatic Cell Hybrids

| Cell Line | Chromosome/ Subchromosomal Region Represented | Human DNA Content |
| --- | --- | --- |
| J1 | chromosome 11 | ~144Mb |
| J1-11 | 11p | ~35Mb |
| J1-2 | 11p15 | ~12Mb |
| J1-4a | 11p15.5-.3 | ~5Mb |
| 78-5F3C | 11p15.4-cen | ~30Mb |
| hybrid 54 | 3p14, 3p25 | ~20Mb |
| PK87-9-132 | 9p21-9q12 | ~30Mb |

The products were generated from RsaI digested template, and IRE-bubble PCRs were conducted with Alu-S and Alu-J as described in Example 3. No IRE-bubble PCR products were apparent from the hamster control. In contrast, even the most reduced of the somatic cell hybrids generated a complex set of amplification products which appeared as a smear by EtBr staining, suggesting that the number of amplified products is so great as to obscure individual bands.

To further assess the possible contribution of hamster sequences to the IRE-bubble product, the products from one of the hybrids, J1-11, (See Table 1)) was used as a hybridization probe against HindIII digested human and hamster genomic DNAs. IRE-bubble PCR product from hybrid J1-11 was labeled with $^{32}P$ by the random-hexamer method (Feinberg and Vogelstein, Anal. Biochem. 132: 6–13, 1983) and hybridized in 50% formamide at 50° C. to the indicated DNAs. No hamster sequences were detectable in the IRE-bubble PCR product. These results demonstrate the species specificity of the IRE-bubble PCR amplification technique.

Example 8—Comparison of IRE-bubble PCR and Inter-IRE PCR Amplification

This example illustrates a comparison of the complexity of amplification products generated by IRE-bubble PCR and products generated by inter-IRE PCR (where both primers are derived from IREs). IRE-bubble and inter-IRE PCR products were generated in parallel from nine different human YACs, with an average insert size of 430 kb, under identical conditions, as described in Example 3. In every case, IRE-bubble PCR resulted in the generation of over ten times the number of individual products as did inter-IRE PCR as visualized on ethidium bromide stained agarose gels. A similar differential complexity was also observed with cosmid DNAs.

Example 9—Flourescence In Situ Hybridization With IRE-bubble PCR Products

This example illustrates that IRE-bubble PCR resulted in increased representation and distribution of amplification products as measured by fluorescence in situ hybridization (FISH) as compared to produces from inter-IRE PCR0 IRE-bubble PCR products from various human-hamster somatic cell hybrids were used as FISH probes on human metaphase spreads. (A) IRE-bubble PCR products from hybrid J1 (see Table 1), a human-hamster hybrid monochromosomal for human chromosome 11, were biotinylated and hybridized to normal R banded human metaphases. The probe was detected with avidin FITC conjugate and pseudocolored yellow. R-banded chromosomes were counterstained with propidium iodide and pseudocolored blue. (B) IRE-bubble PCR products from hybrid PK87-9-132 (see Table 1), containing sequences from human chromosome 9, were biotinylated and detected with avidin-FITC (yellow) on a human R banded background (blue). (C) IRE-bubble PCR products from hybrid J1-4a (see Table 1 ), containing sequences from human 11p15.5-.3 (yellow) were biotinylated and detected with aviden-FITC on a human R banded background (blue). (D) IRE-bubble PCR products from a YAC containing approximately 450kb from human chromosome 3 were biotinylated and detected with avidin-Rhodamine pseudocolored yellow. Three other probes were used to mark the chromosome 3 centromeric repeat (large red signal), the chromosome 8 centromeric repeat (large yellow signal), and the chromosome 3 telomere (small red signal). These probes were hybridized to an EBV transformed cell line bearing a t(3;8) translocation counterstained with DAPI.

In all of the somatic cell hybrids tested, the probes produced a robust staining pattern, highlighting chromosomes/subchromosomal regions which corresponded with the known human DNA content of each hybrid. Notably, the probe which was generated from hybrid J1, which has all of human chromosome 11 (approximately 144 Mb; approximately 1–2% of the human genome), when applied as a FISH probe highlighted the whole of chromosome 11. These results are in contrast to those seen with probes generated by inter-IRE PCR amplification of somatic cell hybrids (Lengauer et al., Human Mol. Gen. 2: 505–512, 1990; Lichter et al., Proc. Nat'l Acad. Sci. USA, 87: 6634–6638, 1990; Graw et al., Somatic Cell and Mol. Gen., 18: 269–284, 1992) and flow sorted chromosomes (Suijkerbuijk et al., Genomics, 13: 355–362, 1992). Such probes often result in a non-uniform staining pattern, presumably reflecting the non-uniform distribution of IRE across the genome and the corresponding limits of inter-IRE PCR.

Example 10—Increased Complexity and Representation Generated By IRE-bubble PCR

This example illustrates that subtle differences in the construction of the PCR template, as well as the orientation and specificity of the IRE primers, contributed to the complexity and representation of the IRE-bubble reaction. By constructing a series of template preparations, each using different restriction digests of the same genomic DNA, the relative linear position of repeat elements within each individual template molecule was varied.

Two individual YAC clones were amplified by IRE-bubble PCR as described in Example 3. Templates were prepared either by AluI or RsaI digestion. PCR reactions were initiated with either Alu-S/Alu-J or Alu-end primers. For a given YAC, each individual template preparation yielded a distinct set of simplified products as viewed on EtBr-stained agarose gels. The distribution of products generated from each preparation of template was further enhanced by varying the specificity and/or orientation of the IRE primer used in the PCR reaction.

Example 11—Generation of a Complex Collection of 11p15 Specific Clones and STSs

This example illustrates the construction of a 576 clone library of IRE-bubble PCR products derived from hybrid J1-2 (See Table 1), representing band p15 on human chromosome 11. IRE-bubble PCR products from hybrid J1-2 were "shotgun" cloned into prepared T-vector as described in Example 4. 576 insert-bearing clones were picked. The inserts corresponding to a random 36 clones from this library, ranging in size from 250–850 bp, were amplified by PCR as described in Example 3 (using Alu-S and Alu-J (in a 4:1 ratio) in conjunction with the bubble primer described above), and visualized on a 1.5% agarose gel. There appeared to be minimal duplication of clones, which is consistent with the anticipated complexity of this library.

Several clones from this library were sequenced and appropriate primers selected for the generation of STSs. One such STS (BA-5) was analyzed on a chromosome 11 somatic cell hybrid mapping panel. The resulting pattern of amplification allowed the assignment of this STS to 11p15.2-1. These data have been confirmed by the positioning of BA-5 within an anchored and well characterized YAC contig of 11p15.

Those skilled in the art will be able to ascertain, using no more than routine experimentation, many equivalents of the specific embodiments of the invention described herein. These and all other equivalents are intended to be encompassed by the following claims.

What is claimed is:

1. A method for amplifying a nucleic acid fragment having an interspersed repetitive element, which method comprises:

cleaving a source nucleic acid having at least one interspersed repetitive element so as to obtain at least one nucleic acid fragment having an interspersed repetitive element, said nucleic acid fragment having a first strand and a second strand;

ligating to at least one said nucleic acid fragment at least one bubble oligonucleotide having a first and a second double stranded portion, each of said double stranded portion flanking a substantially non-complementary portion consisting of a first single strand and a second single strand, to make at least one bubble/nucleic acid unit having a first strand and a second strand, said ligation occurring between one of said double stranded portions of said at least one bubble oligonucleotide and said at least one nucleic acid fragment;

separating said first strand of said unit from said second strand of said unit;

treating said separated strands of said unit with a first oligonucleotide primer that is substantially complementary to at least a portion of said interspersed repetitive element on said first strand of said unit under conditions such that an extension product of said first primer is synthesized which is complementary to said first strand of said unit, said extension product containing a complementary region to at least a part of said first single strand of said bubble oligonucleotide;

treating said separated strands of said unit with a second oligonucleotide primer that is substantially complementary to at least a portion of said extension product of said first primer, said portion of said extension product of said first primer containing sequences complementary to said part of said first single strand of said bubble oligonucleotide, under conditions such that an extension product of said second primer is synthesized which is complementary to said extension product of said first primer;

separating said primer extension products from their complements to produce separated single stranded extension products;

treating said separated single stranded extension products with said first primer and said second primer under conditions such that an extension product is synthesized from each of said separated single stranded extension products.

2. The method of claim 1 wherein the separating said primer extension products step and the treating said separated single stranded extension products step are repeated.

3. A method for amplifying at least one bubble/nucleic acid unit having an interspersed repetitive element derived from a source nucleic acid having an interspersed repetitive element, which method comprises:

providing at least one bubble/nucleic acid unit having a first strand and a second strand, said unit having at least one nucleic acid fragment and at least one bubble oligonucleotide having a first and a second double stranded portion, each of said double stranded portion flanking a substantially non-complementary portion consisting of a first single strand and a second single strand;

separating said first strand of said unit from said second strand of said unit;

treating said separated strands of said unit with a first oligonucleotide primer that is substantially complementary to at least a portion of said interspersed repetitive element on said first strand of said unit under, first conditions such that an extension product of said first primer is synthesized which is complementary to said first strand of said unit, said extension product containing a complementary region to at least a part of said first single strand of said bubble oligonucleotide; and treating said separated strands of said unit with a second oligonucleotide primer that is substantially complementary to at least a portion of said extension product of said first primer, said portion of said extension product of said first primer containing sequences complementary to said part of said first single strand of said bubble oligonucleotide, under second conditions such that an extension product of said second primer is synthesized which is complementary to said extension product of said first primer.

4. The method of claim 3 and further comprising cleaving said source nucleic acid having said interspersed repetitive element to form at least one said nucleic acid fragment having a first strand and a second strand.

5. The method of claim 3 and further comprising ligating to at least one said nucleic acid fragment at least one bubble oligonucleotide, said ligation occurring between one of said double stranded portions of said at least one bubble oligonucleotide and said at least one nucleic acid fragment, to make at least one of said bubble nucleic acid unit.

6. The method of claim 3 and further comprising:

separating said primer extension products from their complements to produce separated single stranded extension products; and treating said separated single stranded extension products with said first primer and said second primer under conditoins such that an extension product is synthesized from each of said separated single stranded extension products.

7. The method of claim 6 wherein the separating step and the treating said separated single stranded extension products step are repeated.

8. The method of claim 3 wherein said source nucleic acid is selected from the group consisting of a somatic cell hybrid, a yeast artificial chromosome clone, a cosmid clone, a bacterial artificial chromosome clone, a P1 artificial chromosome clone a plasmid clone and a phage clone.

9. The method of claim 4 wherein said source nucleic acid is cleaved with a blunt cutting restriction enzyme.

10. The method of claim 3 wherein said first and second double stranded portions of said bubble oligonucleotide each comprise approximately 10 to approximately 50 complementary nucleotides.

11. The method of claim 3 wherein said non-complementary portion of said bubble oligonucleotide comprises two single strands each of approximately 15 to approximately 35 nucleotides.

12. The method of claim 3 wherein said second conditions for treating said units with said second primer are selected so that said second primer is able to hybridize to the complement of said first single strand of said non-complementary portion of said bubble oligonucleotide, but is not able to hybridize to said second strand of said non-complementary portion of said bubble oligonucleotide.

13. The method of claim 3 wherein said first and second conditions in said treating steps for synthesizing said extension products include treating said units with four different nucleoside triphosphates and a template dependent polymerase.

14. The method of claim 13 wherein said polymerase is a thermostable polymerase.

15. The method of claim 3 wherein said interspersed repetitive element is selected from the group consisting of Alu, Line, O, MER, mouse B1 and mouse L1.

16. The method of claim 3 wherein said first primer is selected from the group consisting of sequences represented by Alu-S, Alu-J, Alu-end, 47-23, L1HS, MER1, MER2, MER4 through MER22, B1Mv3CH and B25'notI.

17. The method of claim 3 wherein at least a portion of said first primer consists of human specific repetitive sequences.

18. The method of claim 3 wherein said second primer is approximately 15 to approximately 35 nucleotides.

19. The method of claim 3 wherein said second primer has the sequence:

5'-GCGGCCGCAGTTCGTCAACATAGCATTTCT-3' (Seq. ID No. 7).

20. A bubble oligonucleotide, having a first and a second strand, for ligation to a nucleic acid or a mixture of nucleic acids, comprising:

a first double stranded portion;

a single stranded portion having a first and a second strand adjacent to said first double stranded portion, said first strand of said single stranded portion being substantially non-complementary to said second strand of said single stranded portion;

a second double stranded portion adjacent to said single stranded portion;

said first strand of said bubble oligonucleotide having the nucleotide sequence: 5'CTCTCCCTTCTGCGGCCG-CAGTTCGTCAACATAGCATTTCTGTCCTCTCCT TC-3' (Seq. ID No. 5); and said second strand of said bubble oligonucleotide having the nucleotide sequence: 5'-GAAGGAGAGGACGCT-GTCTGTCGAAGGTAAACGGAC-GAGAGAAGGGA GAG-3' (Seq. ID No. 6).

21. A method for labeling target nucleic acids, which method comprises:

amplifying nucleic acid fragments in accordance with claim 3 so as to obtain a heterogeneous mixture of said nucleic acid fragments;

labeling said heterogeneous mixture of said nucleic acid fragments;

contacting said labeled nucleic acid fragments with said target nucleic acid under conditions such that hybridization occurs between said labeled nucleic acid fragments and said target nucleic acid.

22. The method of claim 21 wherein said target nucleic acid is chromosomal metaphase or interphase nucleic acid.

23. The method of claim 21 wherein substantial portions of said heterogeneous mixture of said nucleic acid fragments have nucleic acid base sequences substantially complementary to said target nucleic acid.

24. The method of claim 21 wherein said labeling is by treating with a compound selected from the group consisting of biotin, digoxigenin, fluorescein and mixtures thereof.

25. The method of claims 21 wherein said labeling is radioactive labeling.

26. The method of claim 21 wherein said hybridization is fluorescence in situ hybridization.

27. A method for detecting the presence or absence of a chromosomal aberration in a nucleic acid of a test organism, which method comprises:

providing nucleic acid from a test organism and nucleic acid from a reference organism;

staining said nucleic acids from said test organism and from said reference organism in accordance with claim 21 so as to produce a pattern of staining of said nucleic acids from said test and reference organisms;

comparing said pattern of staining of said nucleic acids from said test organism with said pattern of staining of said nucleic acids from said reference organism so as to determine the presence or absence of different staining patterns between said test organism and said reference organism; and determining the presence or absence of said chromosomal aberration in said nucleic acid of said test organism based upon the presence or absence of said different staining patterns.

28. The method of claim 27 wherein said chromosomal aberration is selected from the group consisting of duplicated chromosomes, missing chromosomes, duplicated portions of chromosomes, missing portions of chromosomes, breaks, rings, dicentrics, and chromosomal rearrangements.

29. The method of claim 28 wherein said chromosomal rearrangement is selected from the group consisting of translocations, deletions, inversions, amplifications and insertions.

30. The method claim 27 wherein said chromosomal aberration is diagnostic for a condition selected from the group consisting of a genetic disorder, a predisposition to a genetic disorder, a malignant state of a cell and a predisposition to a malignant state of a cell.

31. The method of claim 27 wherein said nucleic acid is derived from cells selected from the group consisting of somatic cells, germ line cells, a tissue, fetal cells, malignant cells and amniotic fluid.

32. A kit for generating IRE-bubble PCR products from a target nucleic acid, which kit comprises, in packaged form, a multicontainer unit having:

a bubble oligonucleotide having a first and a second double stranded portion, each of said double stranded portions flanking a substantially non-complementary portion consisting of a first single strand and a second single strand, said bubble oligonucleotide adapted for ligation to a target nucleic acid fragment;

a bubble primer having a nucleotide sequence so as to be able to hybridize to the complement of said first single strand of said non-complementary portion of said bubble oligonucleotide, but is not able to hybridize to said second strand of said non-complementary portion of said bubble oligonucleotide;

an interspersed repetitive element primer having a nucleotide sequence that is substantially complementary to at least a portion of an interspersed repetitive element, said interspersed repetitive element being present in said target nucleic acid;

each of four different nucleoside triphosphates; and a template dependent polymerase.

33. The kit of claim 32 wherein said multicontainer unit further has a restriction enzyme for cleaving said target nucleic acid to obtain target nucleic acid fragments for ligation to said bubble oligonucleotide.

34. The kit of claim 32 wherein said multicontainer unit further has a T-vector and ligase for cloning of said generated IRE-bubble PCR products.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:1:

GAGGGTTTCA CGACCCTAAT GTCC 24

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:2:

GAGGTTGCAG TGAGCCGAGA T 21

( 2 ) INFORMATION FOR SEQ ID NO:3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:3:

GAGGCTGCAG TGAGCCGTGA T 21

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:4:

ACAGAGYRAG ACTCYRTCTC 20

( 2 ) INFORMATION FOR SEQ ID NO:5:

( i ) SEQUENCE CHARACTERISTICS:

(A) LENGTH: 53 base pairs
(B) TYPE: nucleic acid
(C) STRANDEDNESS: single
(D) TOPOLOGY: linear (xi) SEQUENCE DESCRIPTION: SEQ ID NO:5:

CTCTCCCTTC TGCGGCCGCA GTTCGTCAAC ATAGCATTTC TGTCCTCTCC TTC    53

(2) INFORMATION FOR SEQ ID NO:6:

(i) SEQUENCE CHARACTERISTICS:
(A) LENGTH: 50 base pairs
(B) TYPE: nucleic acid
(C) STRANDEDNESS: single
(D) TOPOLOGY: linear (xi) SEQUENCE DESCRIPTION: SEQ ID NO:6:

GAAGGAGAGG ACGCTGTCTG TCGAAGGTAA ACGGACGAGA GAAGGGAGAG    50

(2) INFORMATION FOR SEQ ID NO:7:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:7:

GCGGCCGCAG TTCGTCAACA TAGCATTTCT    30

(2) INFORMATION FOR SEQ ID NO:8:

(i) SEQUENCE CHARACTERISTICS:
(A) LENGTH: 282 base pairs
(B) TYPE: nucleic acid
(C) STRANDEDNESS: single
(D) TOPOLOGY: linear (xi) SEQUENCE DESCRIPTION: SEQ ID NO:8:

GGCTGGGCGT GGTGGCTCAC ACCTGTAATC CCAGCACTTT GGGAGGCCGA GGTGGGTGGA    60

TCACCTGAGG TCAGGAGTTC AAGACCAGCC TGGCCAACAT GGTGAAACCC CGTCTCTACT    120

AAAAATACAA AAATTAGCCG GGCGTGGTGG CGCGCGCCTG TAATCCCAGC TACTCGGGAG    180

GCTGAGGCAG GAGAATCGCT TGAACCCAGG AGGTGGAGGY TGCAGTGAGC CGWGATCGCG    240

CCACTGCACT CCAGCCTGGG CAACAGAGYR AGACTCYRTC TC    282